ized States Patent (12) United States Patent
Harrison et al.

(10) Patent No.: US 7,949,412 B1
(45) Date of Patent: May 24, 2011

(54) COATED ELECTRODE ARRAY HAVING UNCOATED ELECTRODE CONTACTS

(75) Inventors: William Vanbrooks Harrison, Valencia, CA (US); Michael S Colvin, Newbury Park, CA (US); Janusz A Kuzma, Parker, CO (US); Thomas J Balkany, Coral Gables, FL (US)

(73) Assignee: Advanced Bionics, LLC, Valencia, CA (US)

( * ) Notice: Subject to any disclaimer, the term of this patent is extended or adjusted under 35 U.S.C. 154(b) by 432 days.

(21) Appl. No.: 11/421,742

(22) Filed: Jun. 1, 2006

Related U.S. Application Data (60) Provisional application No. 60/687,495, filed on Jun. 2, 2005.

(51) Int. Cl.
*A61N 1/372* (2006.01)
(52) U.S. Cl. ......... 607/137; 607/116; 607/117; 607/136
(58) Field of Classification Search .................. 607/137, 607/116, 117, 136
See application file for complete search history.

(56) References Cited

U.S. PATENT DOCUMENTS

| | | |
|---|---|---|
| 3,416,531 A | 12/1968 | Edwards |
| 3,572,344 A | 3/1971 | Bolduc |
| 3,924,632 A | 12/1975 | Cook |
| 4,033,355 A | 7/1977 | Amundson |
| 4,355,646 A | 10/1982 | Kallok et al. |
| 4,432,377 A | 2/1984 | Dickhudt |
| 4,437,474 A | 3/1984 | Peers-Trevarton |
| 4,458,695 A | 7/1984 | Peers-Trevarton |
| 4,559,951 A | 12/1985 | Dahl et al. |
| 4,608,986 A | 9/1986 | Beranek et al. |
| 4,640,983 A | 2/1987 | Comte |
| 4,819,647 A | 4/1989 | Byers et al. |
| 4,840,186 A | 6/1989 | Lekholm et al. |
| 4,899,787 A | 2/1990 | Ouchi et al. |
| 4,944,088 A | 7/1990 | Doan et al. |
| 4,991,152 A | 2/1991 | Letiche |
| 5,037,404 A | 8/1991 | Gold et al. |
| 5,057,092 A | 10/1991 | Webster, Jr. |
| 5,095,905 A | 3/1992 | Klepinski |
| 5,383,922 A | 1/1995 | Zipes et al. |
| 5,411,545 A | 5/1995 | Breyen et al. |
| 5,423,881 A | 6/1995 | Breyen et al. |

(Continued)

FOREIGN PATENT DOCUMENTS

EP    1024855 B1    11/2003

(Continued)

*Primary Examiner* — Scott M Getzow
*Assistant Examiner* — Joseph M Dietrich
(74) *Attorney, Agent, or Firm* — Victoria A. Poissant; Mary Elizabeth Bush (57) ABSTRACT

Implantable electrode leads, e.g. cochlear, spinal cord stimulation, or any type of neurostimulation leads, used in a patient's body to stimulate muscle or nerve tissue, provide enhanced stimulation for treating, e.g., hearing loss or chronic pain. One such lead includes, an implantable electrode array, adapted for insertion into a cochlea, which lead provides improved stability of electrode contact direction. In-line electrodes are spaced-apart along one side of a flexible carrier having non-conductive bumps coated with a bioresorbable material spaced apart between each electrode contact. Over time the bioresorbable material is absorbed thereby reducing chronic placement pressure caused during the insertion of the electrode array into the cochlea. The bioresorbable material may also serve as a carrier for drugs or other materials that would improve performance of the electrode for any type of lead.

35 Claims, 5 Drawing Sheets

U.S. PATENT DOCUMENTS

| | | | | |
|---|---|---|---|---|
| 5,443,493 | A | 8/1995 | Byers et al. | |
| 5,578,084 | A | 11/1996 | Kuzma et al. | |
| 5,580,699 | A | 12/1996 | Layman et al. | |
| 5,603,726 | A | 2/1997 | Schulman et al. | |
| 5,630,839 | A * | 5/1997 | Corbett et al. | 607/137 |
| 5,653,742 | A * | 8/1997 | Parker et al. | 607/137 |
| 5,658,263 | A | 8/1997 | Dang et al. | |
| 5,658,709 | A | 8/1997 | Layman et al. | |
| 5,728,063 | A | 3/1998 | Preissman et al. | |
| 5,788,979 | A | 8/1998 | Alt et al. | |
| 5,931,864 | A * | 8/1999 | Chastain et al. | 607/128 |
| 5,938,596 | A | 8/1999 | Woloszko et al. | |
| 5,957,970 | A | 9/1999 | Shoberg et al. | |
| 6,018,683 | A | 1/2000 | Verness et al. | |
| 6,026,567 | A | 2/2000 | Swoyer et al. | |
| 6,052,625 | A | 4/2000 | Marshall | |
| 6,091,979 | A * | 7/2000 | Madsen | 600/377 |
| 6,112,124 | A | 8/2000 | Loeb | |
| 6,129,753 | A | 10/2000 | Kuzma | |
| 6,195,586 | B1 * | 2/2001 | Kuzma | 607/137 |
| 6,208,881 | B1 | 3/2001 | Champeau | |
| 6,304,787 | B1 * | 10/2001 | Kuzma et al. | 607/137 |
| 6,343,226 | B1 | 1/2002 | Sunde et al. | |
| 6,379,353 | B1 | 4/2002 | Nichols | |
| 6,415,187 | B1 | 7/2002 | Kuzma et al. | |
| 6,501,991 | B1 | 12/2002 | Honeck et al. | |
| 6,522,932 | B1 | 2/2003 | Kuzma et al. | |
| 7,146,227 | B2 | 12/2006 | Dadd et al. | |
| 7,272,449 | B2 | 9/2007 | Dadd et al. | |
| 7,294,345 | B2 | 11/2007 | Haapakumpu et al. | |
| 7,406,352 | B2 | 7/2008 | Gibson | |
| 7,451,000 | B2 | 11/2008 | Gibson et al. | |
| 2002/0077685 | A1 | 6/2002 | Sundquist et al. | |
| 2004/0116995 | A1 * | 6/2004 | Dadd | 607/137 |
| 2004/0215306 | A1 * | 10/2004 | Heil et al. | 607/122 |
| 2004/0236390 | A1 * | 11/2004 | Dadd et al. | 607/55 |
| 2005/0186244 | A1 * | 8/2005 | Hunter et al. | 424/423 |
| 2006/0004432 | A1 | 1/2006 | Parker et al. | |
| 2006/0247749 | A1 | 11/2006 | Colvin | |
| 2006/0282123 | A1 | 12/2006 | Hunter et al. | |
| 2006/0287689 | A1 | 12/2006 | Debruyne et al. | |
| 2007/0073130 | A1 * | 3/2007 | Finch et al. | 600/372 |
| 2007/0073371 | A1 | 3/2007 | Dadd et al. | |
| 2007/0179566 | A1 | 8/2007 | Gantz et al. | |
| 2007/0203557 | A1 | 8/2007 | Gantz et al. | |
| 2008/0269864 | A1 | 10/2008 | Dadd et al. | |
| 2009/0043369 | A1 | 2/2009 | Radeloff | |
| 2009/0043370 | A1 | 2/2009 | Gibson et al. | |

FOREIGN PATENT DOCUMENTS

| | | |
|---|---|---|
| EP | 0971660 B1 | 9/2004 |
| EP | 1604626 A2 | 12/2005 |
| EP | 1604626 A3 | 12/2005 |
| EP | 1340408 B1 | 10/2008 |
| EP | 1604626 B1 | 12/2008 |
| EP | 1425940 B1 | 3/2009 |
| EP | 2042137 A1 | 4/2009 |
| WO | 9710784 A1 | 3/1997 |
| WO | 9922806 A1 | 5/1999 |
| WO | 02/28473 A1 | 4/2002 |
| WO | 02/28474 A1 | 4/2002 |
| WO | 0232498 A1 | 4/2002 |
| WO | 0241666 A1 | 5/2002 |
| WO | 0243623 A1 | 6/2002 |
| WO | 02071984 A1 | 9/2002 |
| WO | 03024153 A1 | 3/2003 |
| WO | 2004050056 A1 | 6/2004 |
| WO | 2008031144 A1 | 3/2008 |
| WO | 2008150974 A1 | 12/2008 |
| WO | 2009067764 A1 | 6/2009 |

* cited by examiner

COATED ELECTRODE ARRAY HAVING UNCOATED ELECTRODE CONTACTS

The present application claims the benefit of U.S. Provisional Patent Application Ser. No. 60/687,495, filed Jun. 2, 2005, which application is incorporated herein by reference in its entirety.

BACKGROUND OF THE INVENTION

The teachings of the present disclosure relate to external or implantable stimulation devices, e.g., cochlear prosthesis used to electrically stimulate the auditory nerve, spinal cord stimulation (SCS) devices used to provide therapy along the dura of the spinal cord, or other types of neurostimulation devices used to provide therapy to muscles or nerve tissue. More particularly, the teachings of the present disclosure relate to an implantable electrode array for use with, e.g., a cochlear stimulator, an SCS stimulator, or any type of neurostimulation device used in the body to stimulate muscle or nerve tissue. Such stimulation devices, e.g., cochlear stimulator, are designed to place the electrode contacts of the electrode array generally along one side of the array so that when the array is implanted, e.g., in the cochlea, or other body cavity, the side of the array whereon the electrode contacts are located can be positioned in close proximity to the cells that are to be stimulated, thereby allowing such cells to be stimulated with minimal power consumption.

Furthermore, the teachings of the present disclosure includes electrode arrays which further include a bioresorbable material which improves performance and adds additional benefits to the electrode array. For example, where the array is implanted in the cochlea, the electrode side of the array may be positioned closest to the modiolar wall, thereby placing all of the individual electrode contacts in close proximity to the ganglion cells and thereby in close proximity to the auditory nerve fibers, and in addition, the bioresorbable coated material, in time, could be absorbed and help minimize or eliminate any pressure within the cochlea or other body cavity. When using the electrode array described herein in SCS applications, the electrode array may be placed in a location such that the electrical stimulation will create a tingling sensation felt by the patient known as paresthesia. SCS electrode arrays containing a bioresorbable material will improve performance and add additional benefits to the electrode array and further improve the performance of the SCS stimulation therapy.

The hearing loss phenomenon, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea (the hair cells are located in the vicinity of the radially outer wall of the cochlea) by presenting electrical stimulation to the auditory nerve fibers directly, leading to the perception of sound in the brain and at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6-30 in number. Such electrode array is pushed into the scala tympani duct to a depth of about 20-30 mm via a surgical opening made in the round window at the basal end of the duct. During use, electrical current is passed into the fluids and tissues immediately surrounding the individual electrode contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode array with spiral-shaped carrier shown in the '647 patent represents a significant advance in the art, there exists lack of sufficient shape memory associated with the carrier to allow it to return to its original curvature (once having been straightened for initial insertion) with sufficient hugging force to allow it to wrap snugly against the modiolus of the cochlea.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

Many cochlear electrode arrays of the prior art are made for insertion into a left cochlea, or a right cochlea, depending upon the orientation of the electrode contacts one to another. It would be desirable for a universal electrode array to be made that could be used in either cochlea, left or right, without concern for whether the electrodes were orientated in a right or left side orientation.

During the insertion procedure of the modular hugging electrode, a pressure build-up occurs which may potentially damage the modiolar wall structure of the cochlea. The pressure may become chronic causing discomfort and infection to the patient. It would thus be desirable to have a modiolar hugging electrode that can reduce the pressure buildup after insertion as well as reduce discomfort and infection.

It is thus evident that improvements are still needed in, e.g., implantable cochlear electrodes, particularly to facilitate assembling an electrode so that the electrode contacts are on the medial side of the electrode array, and to better assure that the electrode assumes a close hugging relationship with the modiolus once implantation of the electrode has occurred without the internal pressure that the patient may experience within the cochlea.

Stimulation systems, e.g., cochlear, SCS, cardiac, brain or peripheral nerve stimulation systems, are further enhanced by implementing the teachings of the present disclosure to the electrode array which is part of the system.

SUMMARY OF THE INVENTION

The teachings of the present disclosure addresses the above and other needs by providing a universal electrode array, adapted for insertion into either a left or right cochlea, which provides improved stability of electrode contact direction. All of the electrode contacts are spaced apart along one edge or side of the array, termed the "medial side". The structure of the electrode array facilitates bending of the array with the electrode contacts on the inside of the bend, yet deters flexing or twisting of the array that would tend to position or point the electrode contacts away from the inside of the bend. Hence, when inserted into the scala tympani duct of a cochlea, all of the electrode contacts on the medial side of the array generally face the modiolus wall of the cochlea. Furthermore the electrode side includes a bioresorbable coated material which, over time, is absorbed and thereby reduces pressure buildup within the cochlea.

The term bioresorbable as used herein is intended to encompass the various known biocompatible materials that are resorbed or otherwise degraded over time within the vivo environment. The material composition should be biodegradable in vivo and yield degradation products which are themselves non-inflammatory and non-toxic. Biodegradability is desired to provide a natural resorbable process without the possibility of chronic tissue reaction to the foreign material. The rate of degradation of the material within the cochlea or any part of the body can be controlled by adjusting the yield composition as is known in the art of bioresorbable materials.

In one embodiment, small non-conductive bumps or humps are formed in the carrier between the electrode contact areas on the medial side of the array. These small bumps are made, e.g., from a soft silicone rubber, or equivalent substance. When inserted into the cochlea, the small bumps serve as non-irritating stand-offs, or spacers, that keep the electrode contacts near the modiolus wall, but prevent the electrode contacts from actually touching the modiolus wall. The bumps may also serve as dielectric insulators that help steer the stimulating electrical current in the desired direction, towards the modiolus wall, as taught, e.g., in U.S. Pat. No. 6,112,124, incorporated herein by reference. Furthermore the non-conductive bumps are coated with a bioresorbable material with a defined thickness which, over time, is absorbed to thereby reduce chronic placement pressure which may have been induced during the insertion of the electrode array into the cochlea. The bioresorbable material may also serve as a carrier for drugs and other materials that would improve performance of the electrode array. Such drugs are used to elicit a desired therapeutic or other result, e.g., to inhibit fibrous tissue or bone growth in the vicinity of the electrode contacts; or to promote healing of damaged tissue in the region of the electrode contacts, or to prevent infection and discomfort to the patient.

It is a further feature of the present disclosure described herein to provide an electrode array having non-conductive bumps coated with a bioresorbable material. The bioresorbable material should be non-toxic and have a reliable decomposition and absorption. The bioresorbable material can be any of one of various known materials such as polydioxanone, polycaprolactone, polyhydroxybutyrate, polyamino acid, polymers formed of alpha hydroxy acids, lactic acids, poly-L-lactic acids, polylactic-coglycolic acid polymers, polysaccharides as well as other suitable combinations thereof known in the art of bioresorbable materials. Other examples of bioresorbable materials may include: glycoaminoglycans, hydroxyethyl cellulose, oxidized celluloses, and suitable combinations thereof.

It is an additional feature of the teachings of the present disclosure to provide a bioresorbable material coated on the surface of the non-conductive bumps which may serve as carriers for drugs or other materials that can improve the performance of the electrode array. Representative drugs that may be used to coat the electrode array and/or the individual non-conductive bumps in accordance with this aspect of the teachings of the present disclosure include selected steroids, either naturally occurring or synthetic, or a Neuro-trophin selected to prevent neural degeneration and/or to promote neural regeneration.

It is a further feature of the teachings of the present disclosure to provide an electrode array used in SCS applications which includes a bioresorbable material on the electrode contact side of the electrode array to further enhance the performance of the SCS stimulation therapy.

BRIEF DESCRIPTION OF THE DRAWINGS

The above and other aspects, features and advantages of the present disclosure will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

For illustration purposes, the following description is provided in conjunction with a Cochlear Stimulation (CS) system. Other types of stimulation systems may also be used such as, but not limited to, spinal cord stimulation systems, cardiac stimulation systems, peripheral nerve stimulation systems, brain stimulation systems and microstimulators. The disclosure presented herein, is further directed to implantable leads for use with implantable or external stimulators. The leads include all neurostimulation leads, e.g., cochlear leads, spinal cord stimulation leads, or leads used in the body to stimulate muscle or nerve tissue. One type of lead, used as an exemplary lead described by the present disclosure is a cochlear lead. Thus, the description that follows focuses on such cochlear lead. However, it is to be understood that the principles taught herein are not limited to a cochlear lead, but may be used with a wide variety of leads.

The present disclosure described herein teaches a particular type of implantable electrode array having multiple, in-line, electrode contacts. Here, the term "in-line", used to describe the electrode contacts, means only that the electrode contacts are spaced apart more or less in alignment with the longitudinal axis of a lead. It does not mean that a perfect, straight alignment with the lead axis must be achieved. For example, electrode contacts that zig-zag somewhat with respect to the lead axis would still be considered to be in-line electrodes for purposes of the present disclosure. Thus, in general, "in-line" means that of two adjacent electrode contacts, one will be more distal than the other. Further, all of the in-line electrode contacts will have an exposed surface which, more or less, lies on the same side—the medial side—of the curved electrode.

The electrode array of the present disclosure may be best used with an implantable multichannel pulse generator, e.g., an implantable cochlear stimulator (ICS) of the type disclosed in U.S. Pat. No. 5,603,726, incorporated herein by reference, or other suitable stimulator. It is to be understood, however, that although a cochlear electrode array is hereafter described, having dimensions suitable for insertion into the cochlea, the principles of the present disclosure may be applied to other types of implantable leads for applications other than cochlear stimulation.

The electrode array of the present disclosure is particularly adapted to bend or flex in one direction, thereby making it suitable for insertion into a curved body cavity, such as the cochlea.

The teachings of the present disclosure provide an electrode array wherein all of the active electrode contacts of the array are generally positioned along one side, e.g., the medial side (the inside of the curve or bend), of the array. Thus, when inserted into the curved or spiraling cochlea, which may be either a left or right cochlea, wherein the cells to be stimulated are located within the center modiolus wall, the electrode contacts are positioned proximate the modiolus wall, where they are closest to the cells to be stimulated. Hence, the electrode array of the present disclosure facilitates stimulation of the desired cells at lower power levels than would otherwise be needed if the electrode contacts were not proximate the modiolus wall.

Another feature of the electrode array of the present disclosure is that the electrode contacts have a relatively large exposed electrode surface area that is generally planar or flat having a desired geometric shape, e.g., rectangular, semicircular, or oval. However, it is to be understood that the principles of the present disclosure may also be practiced with electrodes that have exposed surface areas that are not flat, e.g., dimpled, or corrugated, or pitted, and that may have an exposed surface area that has irregular geometric shapes.

Except as noted herein, the materials from which the electrode array is made, and the manner of making the electrode array, may be conventional, as are known in the art.

Figure 1:
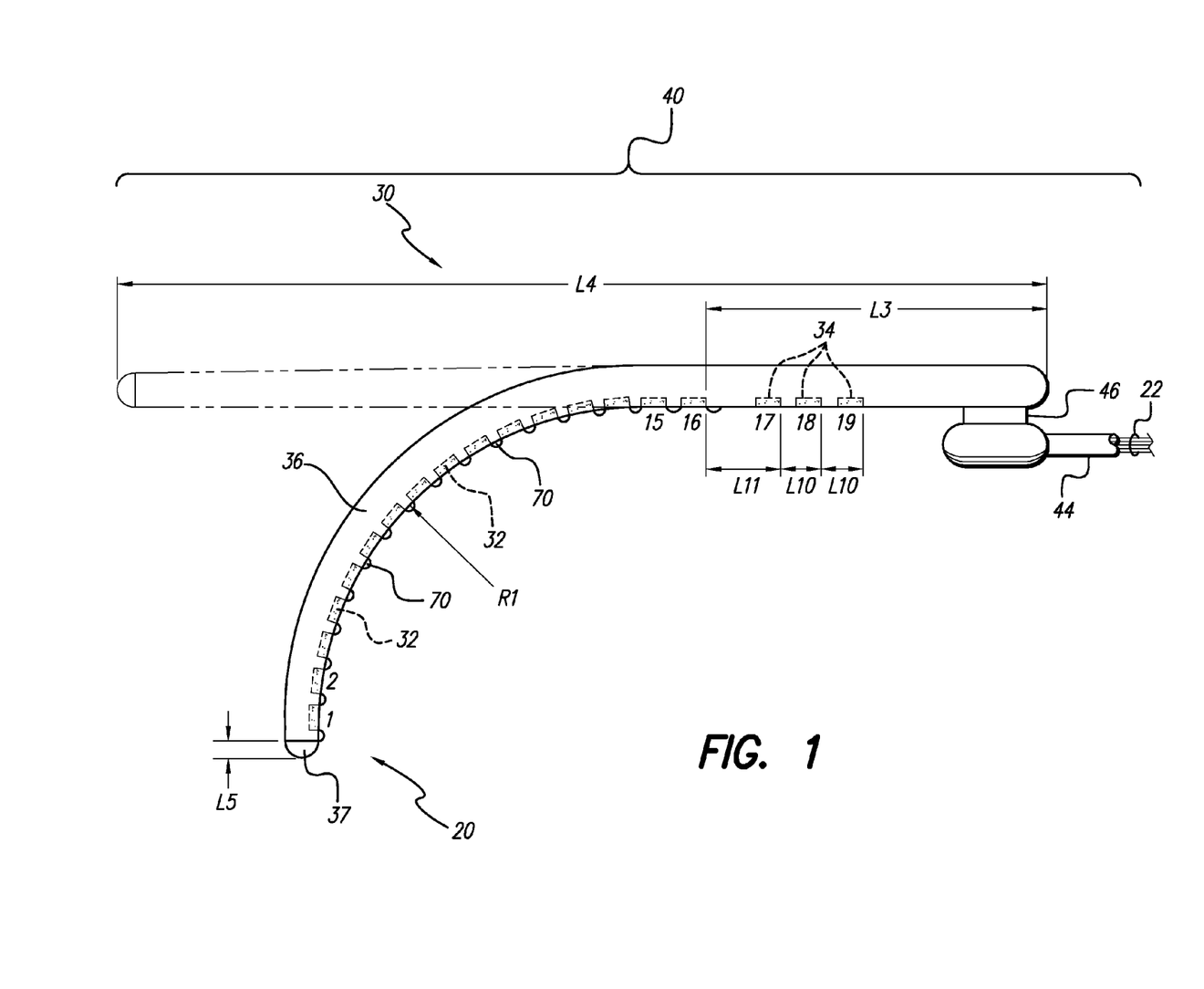
FIG. 1 shows an exemplary embodiment of the electrode array, as presented in the teachings of the present disclosure, wherein bumps are formed in the space between each electrode contact.

An electrode array 30 in accordance with the present disclosure is shown in FIG. 1. The electrode array 30 forms the distal end of a lead/array assembly 40 adapted to be connected to an implantable cochlear stimulator (ICS), not shown. The lead/array assembly 40 includes the electrode array 30, a proximal connector (not shown), and a lead body 44 connecting the array 30 to the proximal connector, wherein the ICS is connected to the proximal connector. The ICS is typically housed within a ceramic or other case, such as is disclosed in U.S. Pat. No. 4,991,152, incorporated herein by reference.

The teachings of the present disclosure are directed to the electrode array 30 at the distal end 20 of the lead/assembly 40. It should be emphasized that the electrode array 30 may be used with any type of proximal connector that interfaces with an appropriate pulse generator.

As seen in FIG. 1, the electrode array 30 is curved an appropriate amount. A multiplicity of in-line electrode contacts 32 are spaced apart so as to lie on the medial side (inside of the curve) of the array. The multiplicity of in-line electrodes comprises n electrodes, where n is an integer of at least 8. The most distal electrode comprises a first electrode, and the most proximal electrode comprises an nth electrode. Sixteen such electrode contacts 32 are used in an exemplary embodiment of the array 30, shown in FIG. 1. These electrode contacts are respectively connected to the wire conductors 22 embedded within the lead. The wire conductors 22 comprises at least n+1 wires, at least one wire being connected to each of the second through nth electrodes, and at least two wires being connected to the first electrode. The most distal electrode contact 32 is connected to a respective wire conductor 22 within the lead 44. The second-most distal electrode contact 32 is also connected to a respective wire conductor 22 within the lead 44. In this manner, the two-most distal electrode contacts 32 on the array 30 may be connected to the first channel of the implantable pulse generator. In a similar manner, the two most proximal electrode contacts 32 on the array 30 are connected to respective wire conductors 22 within the lead 44, and are connected to their corresponding channel, of the implantable pulse generator. The other electrode contacts 32 included within the array 30 are similarly connected to a corresponding channel within the pulse generator, as depicted in, e.g., U.S. Pat. No. 6,129,753. The '753 patent is incorporated herein by reference. Other connections known in the art may also be used.

As further seen in FIG. 1, the electrode array 30 also includes three reference electrode contacts 34, identified in FIG. 1 by the electrode numbers 17, 18 and 19. Such reference contacts 34 are not connected to any wire conductors within the lead 44, and for this reason are sometimes referred to as "dummy reference contacts". Rather, each of these reference contacts 34 may provide a reference indicator or marker to the physician inserting the electrode array relative to the depth of insertion.

As also seen in FIG. 1, the lead/array assembly 40 further includes an offset portion 46 that effectively marks the end of the lead 44 and the beginning of the electrode array 30. Such offset portion 46 facilitates insertion of the electrode array 30 into the scala tympani duct of the cochlea.

Insertion of the electrode array into the cochlea may be performed in conventional manner, e.g., using the electrode insertion tool described in U.S. Pat. No. 5,443,493, incorporated herein by reference. Equivalent or similar insertion tools may also be used.

The material from which the lead/array 40, including the electrode array 30, is made may be any suitable biocompatible material commonly used with implantable leads and other implantable components as is known in the art. A suitable material, for example, is a type of silicone polymer or rubber known as LSR-70 or LSR-25. The properties of LSR-70 and LSR-25 are well known in the art, and LSR-70 and LSR-25 may be obtained commercially from numerous sources, LSR-70 is formed into a desired shape by injecting or otherwise inserting it into a mold while in a liquid state and allowing it to cure in the mold at a specified temperature for a specified time period. For example, LSR-70 may cure at a temperature of 140 degrees C. for about 15 minutes. LSR-25 may likewise be formed into a desired shape using a similar molding process, or it may be applied through a suitable applicator, e.g., a syringe, to a desired area and then formed into a desired shape. LSR-25 is essentially the same as LSR-70 except that when it cures it is significantly softer, i.e., more pliable. Both LSR-70 and LSR-25 readily adhere to the tubing mold so that when cured they become integral therewith.

The electrode array 30 includes electrode array contacts 32 spaced along a medial side of a flexible carrier 36. The flexible carrier 36 is made from, e.g., LSR-70, and is molded around an assembly of electrode contacts 32 and interconnecting conductive wires 22. The electrode array 30 has an overall length L4. Such length L4 is most easily measured when the array 30 is straightened, as shown by the dotted lines in FIG. 1. In one embodiment, L4 has a value of approximately 25 mm. While the electrode array 30 could be formed to assume any desired shape, in one exemplary embodiment, shown in FIG. 1, it is formed to include a natural curve having a radius of curvature R1, with the electrode contacts 32 being positioned along the inside of the curve. The radius of curative R1 may have a value of approximately 9.0 mm.

As further seen in FIG. 1, a soft tip 37, having a depth of distance L5, is typically formed from LSR-25 at the very distal tip of the electrode array 30. In the exemplary embodiment shown in FIG. 1, L5 has a value of approximately 0.3 mm.

As additionally illustrated in FIG. 1, the reference marker contacts 34, identified as electrodes 17, 18 and 19, are spaced from the active electrode 16 a distance L11, with a spacing between the reference marker electrodes of L10. In the exemplary embodiment shown in FIG. 1, the distance L11 is about 3.0 mm, and the distance L10 is about 1.0 mm.

A series of small non-conductive bumps, or humps 70, are formed between the electrode contact areas 32. As seen best in FIG. 2B, these humps 70 have a height H1 of about 0.10 mm to 0.20 mm, e.g., about 0.13 mm, and as seen best in FIG. 2A, have a width W2 of about 0.10 mm to 0.30 mm, e.g., about 0.25 mm. As further seen best in FIG. 1, the humps 70 extend out from the medial surface of the electrode array. The humps 70 are made from a soft silicone rubber, or equivalent substance, such as LSR-25. When inserted into the cochlea, the small bumps 70 serve as non-irritating stand-offs, or spacers, that allow the electrode contacts 32 to be positioned near the modiolus wall, but prevent the electrode contacts 32 from actually touching the modiolus wall. The humps 70 further serve as dielectric insulators that help steer the stimulating electrical current, flowing to or from the electrode contacts, in the desired direction, from or towards the cells located in the modiolus wall, as taught, e.g., in U.S. Pat. No. 6,112,124, incorporated herein by reference.

The teachings of the present disclosure provide an electrode array that is easy and relatively inexpensive to manufacture. One exemplary method of making the electrode array 30 is illustrated, for example, in U.S. Pat. No. 6,129,753, incorporated herein by reference. It is to be emphasized that the method of making the electrode array depicted in the '753 patent is not the only way an electrode array 30 could be made. However, the '753 patent represents an easy and inexpensive way to make the electrode array 30.

Figure 2A:
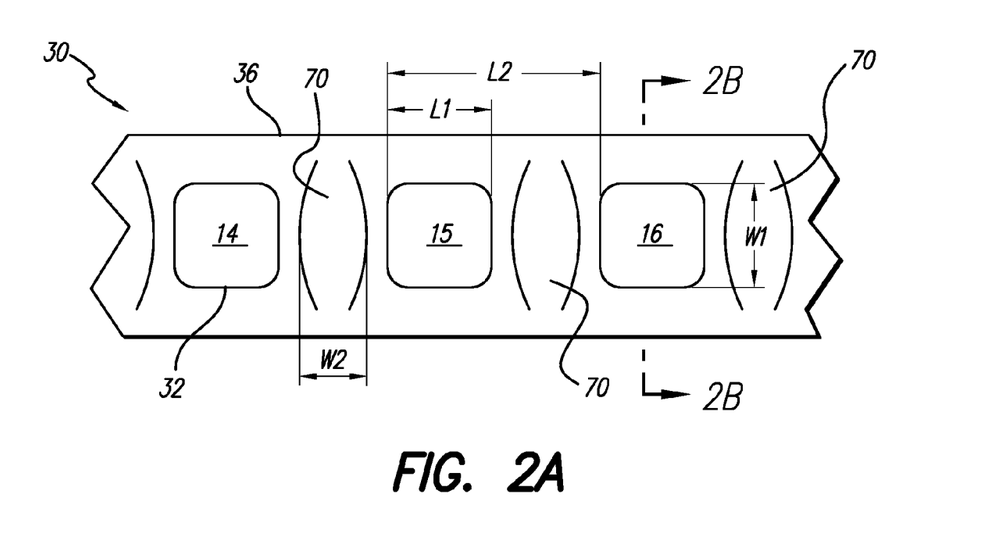
FIG. 2A shows a detail plan view depicting the medial side of the electrode array of FIG. 1.

Referring next to FIG. 2A, exemplary spacing between the individual electrode contacts 32 is depicted. Such spacing, as well as all the other dimensional detail presented herein, is exemplary of a cochlear electrode, and is not intended to be limiting. As seen in FIG. 2A, each exposed electrode contact surface area comprises a generally rectangular-shaped area having a length L1 and a width W1. Other shapes could also be used. In one exemplary embodiment, the rectangular area is roughly a square, with L1 and W1 each having a value of approximately 0.4 mm±10%, thereby providing an exposed electrode surface area of approximately 0.16 mm$^2$. The spacing between corresponding points of adjacent electrode contact areas 32 is a distance L2. L2 has a nominal value of approximately 0.9 mm±0.1 mm.

The electrode contact areas comprise an exposed surface of an electrode contact 32 that is formed from folded strips 210 and 220 (shown in FIG. 2B) of a biocompatible metal, such as platinum, as described more fully below in conjunction with the '753 previously referenced patent. Such electrode contacts are embedded within the molded carrier 36 as illustrated in the sectional view of FIG. 2B, which is taken along the lines 2A-2A of FIG. 2. As seen in FIG. 2A, the carrier 36 is formed to have a cross-sectional area that is generally rectangular, having dimensions of X by Y mm, where the values of X and Y vary as a function of where along the length of the carrier the cross section is viewed. At electrode 16 (near the proximal end of the electrode/array 30), for example, X and Y are both about 0.8 mm. At electrode 1 (near the distal tip of the electrode array), X and Y are both about 0.6 mm. Thus, it is seen that the carrier 36 is tapered along its length so that it has a smaller cross section at its distal tip than it does at its proximal end.

Figure 2B:
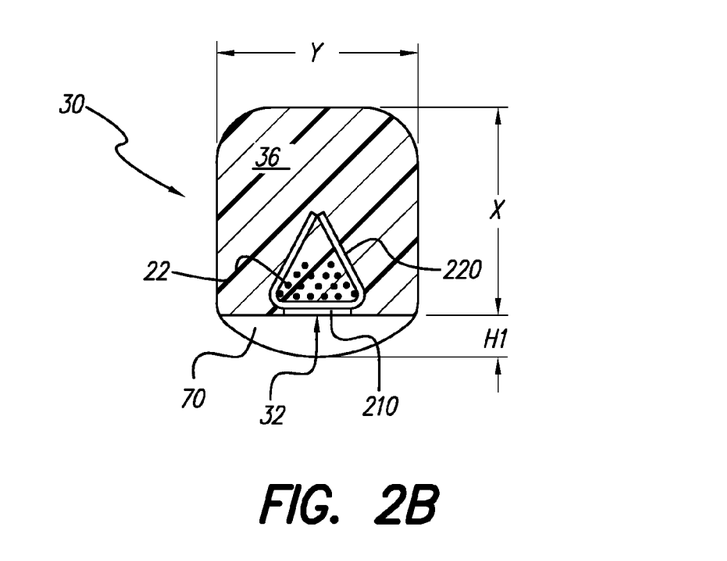
FIG. 2B is a sectional view of the electrode array taken along the line 2B-2B of FIG. 2A.

The structure of the electrode array 30, as seen best in FIG. 1 and also seen in the sectional view of FIG. 2B, bends or flexes more easily in the medial direction than in the lateral direction. That is, the electrode array, with its slight curved shaped, when inserted into the cochlea, is able to bend, as required, to follow the scala tympani duct of the cochlea (whether the right or left cochlea) as it is inserted deeper and deeper into such duct. As it does so, the electrode contacts 32 remain closest to and facing the modiolus wall, as desired. As the electrode array is inserted deeper into the cochlea, the electrode array does not easily twist, or bend laterally, which twisting or bending could move the electrode contacts away from the modiolus wall. This is because the electrode array is inherently stiffer in the lateral direction than in the medial direction due primarily to the presence of the wire bundles and folded/bent electrode contacts which provide an added degree of stiffness in the lateral direction.

To further understand one mechanism by which the teachings of the present disclosure achieves flexing or bending in the medial direction, but resists such bending in a lateral direction (where the "medial" direction may be defined as the direction in which the electrode contacts face, and the "lateral direction" may be defined as a direction perpendicular to both the medial direction and a longitudinal axis of the array), consider the following simplified model of the electrode array: The electrode contacts 32 may be viewed as rigid rectangular plates, hinged together by the flexible carrier material between each plate. Thus, sixteen such plates are hinged together in a long chain, each plate in the chain being connected to an adjacent plate in the chain by way of a hinged connection. Such chain of "hinged plates" may readily pivot about their respective hinged connections, thus easily and readily allowing the chain of hinged plates to bend in the medial direction. However, due to the rigid nature of each plate, bending in the lateral direction, assuming a perfect hinged connection, is virtually impossible. Even assuming a less-than-perfect hinged connection, bending in the lateral direction is still made difficult. This is because fixed-length wire bundles are embedded in the carrier on opposite lateral sides of the array. These "matched" (of equal length) wire bundles tend to make lateral bending or flexing more difficult because such lateral flexing or bending would typically require that one of the wire bundles increase in length, as the other decreases in length, as a lateral bend is made.

Because the electrode contacts of the electrode array disclosed herein remain facing and closest to the modiolus wall, stimulation of the cells embedded within the modiolus wall may occur at lower energy settings than would be required if the electrode contacts were not facing closest to the modiolus wall. Hence, use of the present electrode array allows desired stimulation to be achieved at lower power levels. Lower power levels, in turn, mean that the overall cochlear stimulation system may operate on less power, which usually means a longer interval between battery replacement.

Figure 3:
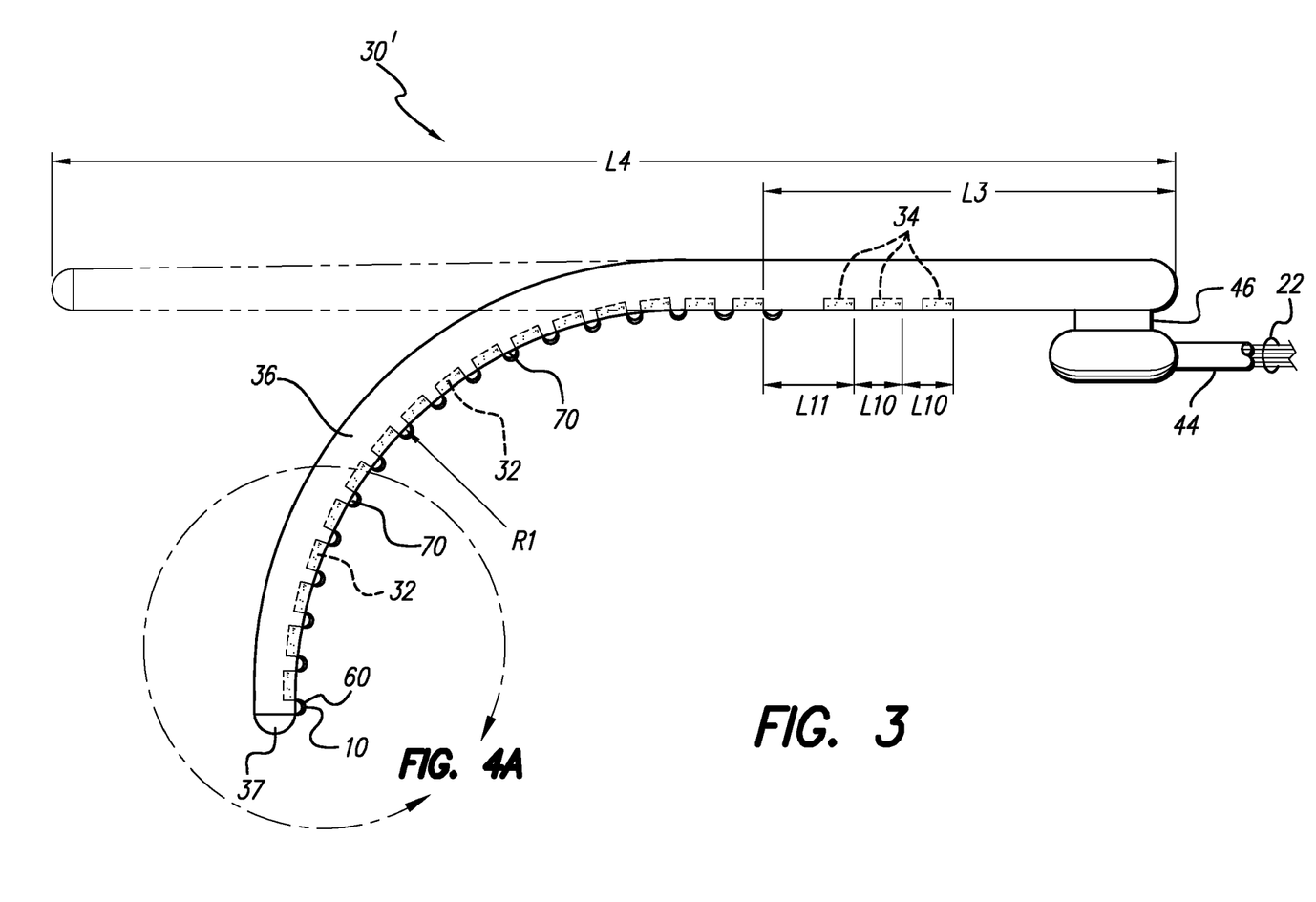
FIG. 3 shows another exemplary embodiment of the electrode array of the teachings of the present disclosure, wherein bumps are formed in the space between each electrode contact and each bump is coated with a bioresorbable material.
Figure 4A:
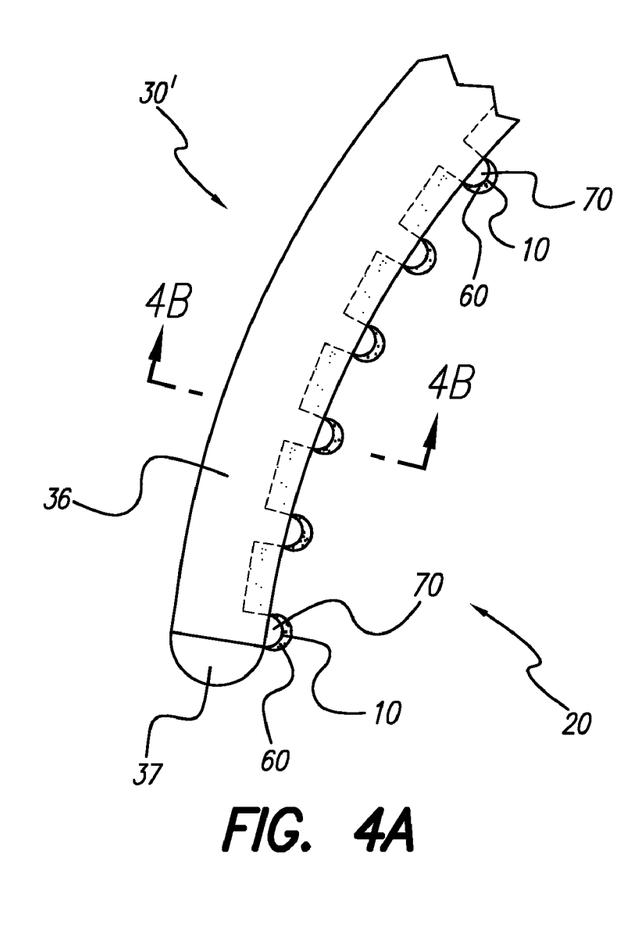
FIG. 4A shows a detail view of the distal end of the electrode array of FIG. 3.
Figure 4B:
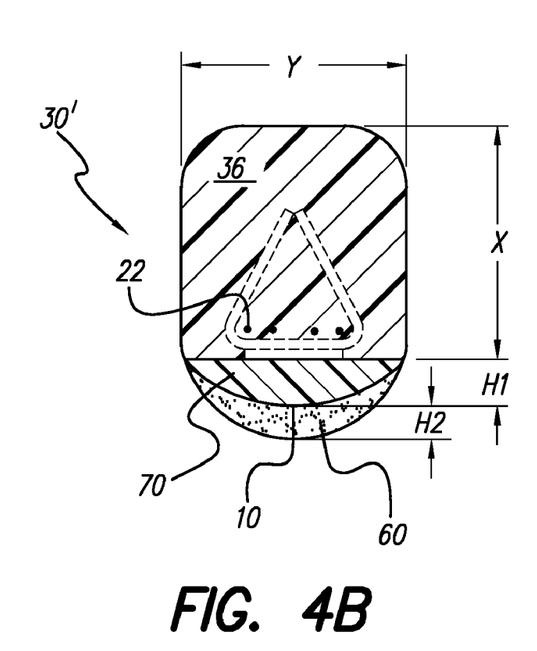
FIG. 4B is a sectional view of the electrode array taken along the line 4B-4B of FIG. 4A.

An electrode array 30' made in accordance with another exemplary embodiment of the present disclosure is shown in FIGS. 3, 4A and 4B. This electrode array 30' is the same as the array 30 illustrated in FIGS. 1, 2A and 2B with the exception that a series of small non-conductive bumps, or humps 70, are formed between the electrode contact areas 32, and each non-conductive bump 70 is coated with a bioresorbable material of defined thickness. The term bioresorbable as used herein is intended to encompass the various known biocompatible materials that are resorbed or otherwise degraded over time within the in vivo environment.

A detail view of the distal end of the electrode array 30' is shown in FIG. 4A where the bumps 70 are clearly shown having a surface 10 coated with a bioresorbable material 60. FIG. 4B shows a cross sectional view taken along line 4B-4B of FIG. 4A. As shown in FIG. 4B, the carrier 36 is depicted having non-conductive bumps 70 having a height H1 of about 0.10 mm to 0.20 mm, e.g., about 0.13 mm; and a bioresorbable material 60, coated on surface 10, having a thickness H2 between about 10 μm and 30 μm build-up, e.g., about 20 μm.

The bioresorbable material 60 along with the non-conductive bumps 70 are used to structurally fill the spacing between the contacts 32 in their predetermined in-line spacial orientation. The bioresorbable material 60 should be non-toxic and have a reliable decomposition and absorption. The bioresorbable material 60 can be any of one of various known materials such as polydioxanone, polycaprolactone, polyhydroxybutyrate, polyamino acid, polymers formed of alpha hydroxy acids, lactic acids, poly-L-lactic acids, polylactic-coglycolic acid polymers, polysaccharides as well as other suitable combinations thereof known in the art of bioresorbable materials. Other examples of bioresorbable materials may include: glycoaminoglycans, hydroxyethyl cellulose, oxidized celluloses, and suitable combinations thereof.

The bioresorbable material 60 coated on surface 10 of the non-conductive bumps 70 may also serve as carriers for drugs or other materials that can improve the performance of the electrode array 30. Representative substances or compounds that may be used to coat the electrode array and/or the individual non-conductive bumps include selected steroids, either naturally occurring or synthetic, or a Neuro-trophin selected to prevent neural degeneration and/or to promote neural regeneration.

As described above, it is thus seen that the teachings of the present disclosure described herein provide an electrode array that is easy to manufacture and which provides enhanced performance when used. Such electrode array provides an array of spaced-apart electrodes along the medial side of the array. Upon insertion into the cochlea, the electrode contacts 32 and the non-conductive bumps 70 all face the modiolus wall. The non-conductive bumps 70 may be coated with a bioresorbable material 60 on surface 10, wherein over time the material is absorbed and aid to eliminate the chronic placement pressure induced during the insertion of the electrode array into the cochlea. The bioresorbable material 60 may also serve as a drug to reduce infection and promote bone growth.

The composition and makeup of the electrode array 30 or 30' makes it easier to bend in the medial direction than in a sideways or lateral direction. Thus, the electrode contacts 32 remain on the medial side of the electrode, which medial side remains closest to the modiolus wall when the electrode is inserted into the cochlea.

Figures 5A, 5B:
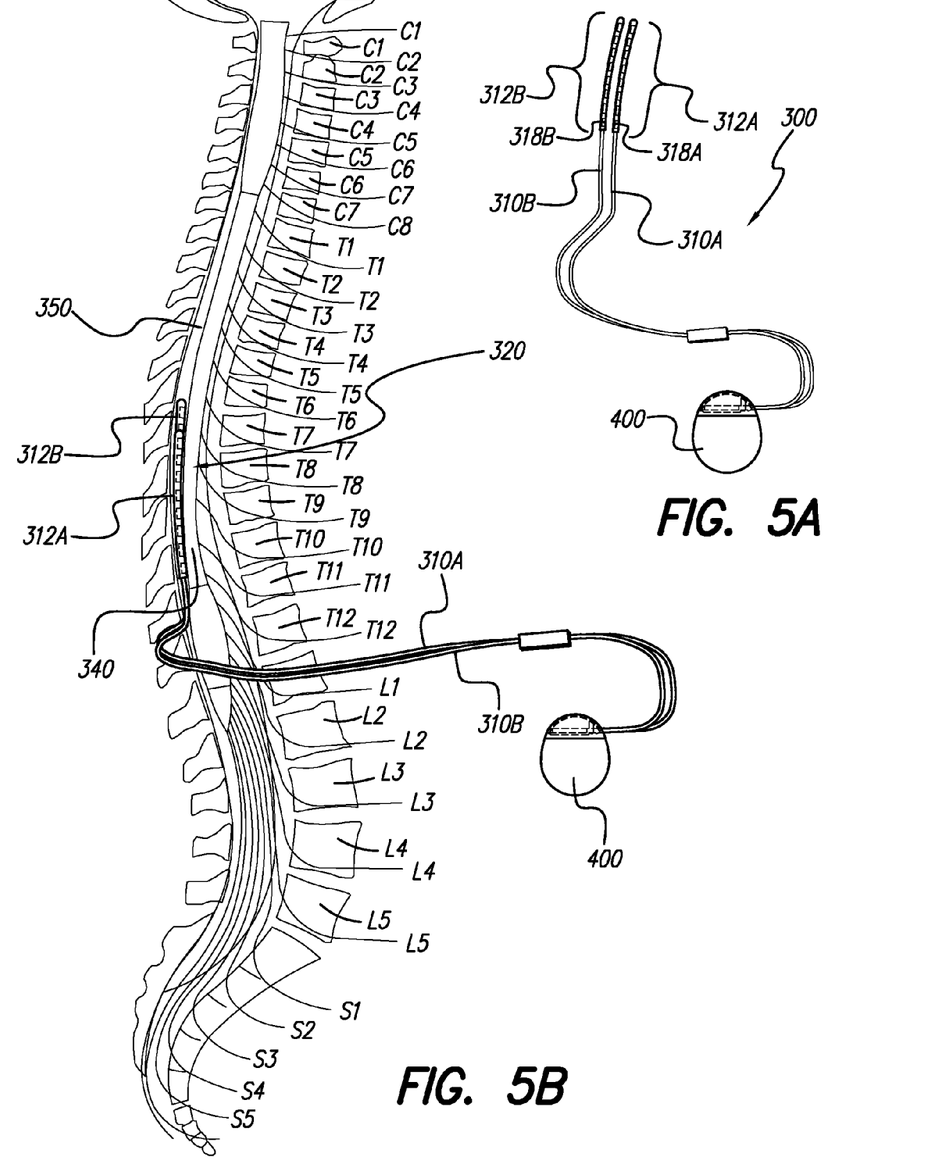
FIG. 5A shows a Spinal Cord Stimulation (SCS) system having an exemplary dual electrode lead system.
FIG. 5B depicts the SCS system of FIG. 5A implanted to stimulate tissue near a spinal column.

The teachings of the present disclosure described above, may also be used for example with a spinal cord stimulation (SCS) system. An exemplary SCS system 300 is shown in FIG. 5A which includes a dual lead system 310A and 310B, both connected, at the proximal end, to a pulse generator 400. At the distal end, the lead system 310A includes an electrode array 312A and the lead system 310B includes an electrode array 312B.

The SCS system 300 shown in FIG. 5A, is depicted implanted in the epidural space 350 shown in FIG. 5B. The set of electrode arrays 312A and 312B are implanted at the site of nerves that are the target of stimulation, e.g., along the spinal cord 340. During the insertion process, the side 320 of the arrays 312A and 312B, whereon the series of electrode contacts 318A and 318B are located, can be positioned in close proximity to the spinal cord 340 and surrounding nerve area. Due to the lack of space near the location where the electrode leads 310A and 310B exit the spinal column, the IPG 400 is generally implanted in the abdomen, above the buttocks, or other suitable location. To further improve the stimulation therapy, a bioresorbable material, as previously described above, is added to the side 320 of the electrode arrays 312A and 312B (in areas where the electrode contacts 318A and 318B are not located). The bioresorbable material thereby enhances the performance of the spinal cord stimulation system 300 which, in time, is absorbed and helps minimize or eliminate any pressure within the epidural space 350. The bioresorbable material may further enhance the therapy the patient receives from the SCS system 300 by providing, e.g., drug therapy, bone growth, and chronic pain relief.

While the invention herein disclosed has been described by means of specific embodiments and applications thereof, numerous modifications and variations could be made thereto by those skilled in the art without departing from the scope of the invention set forth in the claims.

What is claimed is:

1. An implantable device comprising:
    a lead having an electrode array at a distal end, the electrode array having a medial surface on which are located a plurality of spaced apart exposed electrode contacts; and
    a coating of bioresorbable material positioned on the medial surface of the electrode array at one or more locations other than where the electrode contacts are positioned such that the electrode contacts remain uncoated, wherein the coating of bioresorbable material is configured to be absorbed over time to reduce chronic pressure following lead implantation.

2. The implantable device of claim 1 wherein the bioresorbable material is selected from the group consisting of: polydioxanone, polycaprolactone, polyhydroxybutyrate, polyamino acid, polymers formed of alpha hydroxy acids, lactic acids, poly-L-lactic acids, polylactic-coglycolic acid polymers, polysaccharides, and suitable combinations thereof.

3. The implantable device of claim 1 wherein the bioresorbable material is selected from the group consisting of: glycoaminoglycans, hydroxyethyl cellulose, oxidized celluloses, and suitable combinations thereof.

4. The implantable device of claim 1 wherein the bioresorbable material serves as a carrier for a steroid.

5. The implantable device of claim 1 wherein the bioresorbable material serves as a carrier for a neuro-trophin.

6. The implantable device of claim 1 wherein the bioresorbable material has a thickness of H2, wherein H2 is between 10 μm and 30 μm.

7. The implantable device of claim 6 wherein H2 is 20 μm.

8. The implantable device of claim 1 wherein the electrode array comprises an implantable cochlear electrode array adapted for insertion into a cochlea of a patient.

9. The implantable device of claim 1 further comprising a hump formed on the medial side of the array in the space between the exposed electrode contacts, wherein the hump is coated with the bioresorbable material.

10. An implantable electrode array for use with a tissue stimulation device comprising:
    a flexible carrier having a medial side;
    a multiplicity of in-line electrodes having an exposed surface area only on the medial side of the flexible carrier;
    a multiplicity of wires embedded within the flexible carrier, at least one wire of the multiplicity of wires being electrically and physically connected to a respective in-line electrode; and
    a hump formed on the medial side of the array in the space between the exposed surface area of each electrode, wherein the hump is coated with a bioresorbable material such that the electrode contacts remain uncoated, wherein the coating of bioresorbable material is configured to be absorbed over time to reduce chronic pressure following lead implantation; and
    wherein the electrode array is more flexible in a medial direction than in a direction lateral to the medial direction, where the medial direction comprises the direction faced by the exposed contact surface area of the in-line electrodes.

11. The implantable electrode array of claim 10 wherein the multiplicity of in-line electrodes comprises n electrodes, where n is an integer of at least 8, and wherein a most distal electrode comprises a first electrode, and wherein a most proximal electrode comprises an nth electrode.

12. The implantable electrode array of claim 11 wherein the multiplicity of wires comprises at least n+1 wires, at least one wire being connected to each of the second through nth electrodes, and at least two wires being connected to the first electrode.

13. The implantable electrode array of claim 10 further including a tip at the distal end of the electrode array made from a material that is softer than the flexible carrier.

14. The implantable electrode array of claim 10 wherein the flexible carrier is made from a silicone rubber material of a first hardness, and the humps are made from a silicone rubber material of a second hardness, where the first hardness is harder than the second hardness.

15. The implantable electrode array of claim 10 wherein the electrode array comprises an implantable cochlear electrode array adapted for insertion into a cochlea of a patient.

16. The implantable electrode array of claim 10 wherein the bioresorbable material is selected from the group consisting of: polydioxanone, polycaprolactone, polyhydroxybutyrate, polyamino acid, polymers formed of alpha hydroxy acids, lactic acids, poly-L-lactic acids, polylactic-coglycolic acid polymers, polysaccharides, and suitable combinations thereof.

17. The implantable electrode array of claim 10 wherein the bioresorbable material is selected from the group consisting of: glycoaminoglycans, hydroxyethyl cellulose, oxidized celluloses, and suitable combinations thereof.

18. The implantable electrode array of claim 10 wherein the bioresorbable material serves as a carrier for a steroid.

19. The implantable electrode array of claim 10 wherein the bioresorbable material serves as a carrier for a neuro-trophin.

20. The implantable electrode array of claim 10 wherein the bioresorbable material has a thickness of H2, wherein H2 is between 10 μm and 30 μm.

21. The implantable electrode array of claim 20 wherein H2 is 20 μm.

22. An implantable device comprising:
    a lead having an electrode array at a distal end, the electrode array having a plurality of spaced apart exposed electrode contacts; and a coating of bioresorbable material positioned on an outer surface of the contact side of the electrode array at one or more locations other than where the electrode contacts are positioned such that the electrode contacts remain uncoated, wherein the coating of bioresorbable material is configured to be absorbed over time to reduce chronic pressure following lead implantation.

23. The implantable device of claim 22 wherein the bioresorbable material is selected from the group consisting of: polydioxanone, polycaprolactone, polyhydroxybutyrate, polyamino acid, polymers formed of alpha hydroxy acids, lactic acids, poly-L-lactic acids, polylactic-coglycolic acid polymers, polysaccharides, and suitable combinations thereof.

24. The implantable device of claim 22 wherein the bioresorbable material is selected from the group consisting of: glycoaminoglycans, hydroxyethyl cellulose, oxidized celluloses, and suitable combinations thereof.

25. The implantable device of claim 22 wherein the bioresorbable material serves as a carrier for a steroid.

26. The implantable device of claim 22 wherein the bioresorbable material serves as a carrier for a neuro-trophin.

27. The implantable device of claim 22 wherein the bioresorbable material has a thickness of between 10 μm and 30 μm.

28. An implantable device comprising:
a lead having an electrode array at a distal end, the electrode array having a plurality of spaced apart exposed electrode contacts; and
a coating of bioresorbable material positioned on an outer surface of the distal end of the lead at one or more locations other than where the electrode contacts are positioned such that the electrode contacts remain uncoated, wherein the coating of bioresorbable material is configured to be absorbed over time to reduce chronic pressure following lead implantation.

29. The implantable device of claim 28 wherein the bioresorbable material is selected from the group consisting of: polydioxanone, polycaprolactone, polyhydroxybutyrate, polyamino acid, polymers formed of alpha hydroxy acids, lactic acids, poly-L-lactic acids, polylactic-coglycolic acid polymers, polysaccharides, and suitable combinations thereof.

30. The implantable device of claim 28 wherein the bioresorbable material is selected from the group consisting of: glycoaminoglycans, hydroxyethyl cellulose, oxidized celluloses, and suitable combinations thereof.

31. The implantable device of claim 28 wherein the bioresorbable material serves as a carrier for a steroid.

32. The implantable device of claim 28 wherein the bioresorbable material serves as a carrier for a neuro-trophin.

33. The implantable device of claim 28 wherein the bioresorbable material has a thickness of between 10 μm and 30 μm.

34. The implantable device of claim 28 wherein the electrode array has a thickness of between about 0.6 mm and about 0.8 mm.

35. The implantable device of claim 28 wherein the exposed electrode contact has a width of approximately 0.4 mm±10%.

* * * * *